(12) United States Patent
Bostrom et al.

(10) Patent No.: US 11,266,563 B2
(45) Date of Patent: Mar. 8, 2022

(54) EXTENDABLE PENILE IMPLANT (71) Applicant: Boston Scientific Scimed, Inc., Maple Grove, MN (US)

(72) Inventors: John Anders Bostrom, Saint Paul, MN (US); James Ryan Mujwid, Hudson, WI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 76 days.

(21) Appl. No.: 16/597,314

(22) Filed: Oct. 9, 2019

(65) Prior Publication Data
US 2020/0113775 A1 Apr. 16, 2020

Related U.S. Application Data (60) Provisional application No. 62/745,861, filed on Oct. 15, 2018.

(51) Int. Cl.
*A61F 2/26* (2006.01)
*A61H 19/00* (2006.01)

(52) U.S. Cl.
CPC .................... *A61H 19/44* (2013.01)

(58) Field of Classification Search
CPC ................... A61F 2250/0007; A61F 2/26
See application file for complete search history.

(56) References Cited

U.S. PATENT DOCUMENTS

| 4,619,251 A | 10/1986 | Helms et al. |
| 4,628,912 A * | 12/1986 | Fischell ............... A61F 2/26 600/40 |
| 4,730,607 A | 3/1988 | Fischell |
| 10,980,638 B2 | 4/2021 | Diloreto et al. |
| 2008/0103353 A1 | 5/2008 | Jahns et al. |
| 2009/0132044 A1 | 5/2009 | George et al. |
| 2012/0157764 A1 | 6/2012 | Borgaonkar et al. |

FOREIGN PATENT DOCUMENTS

| WO | 2010016905 A1 | 2/2010 |
| WO | 2010087769 A1 | 8/2010 |
| WO | 2018129267 A1 | 7/2018 |

OTHER PUBLICATIONS

Invitation to Pay Additional Fees for PCT Application No. PCT/US2019/055661, dated Jan. 27, 2020, 12 pages.

* cited by examiner

*Primary Examiner* — Christine H Matthews
(74) *Attorney, Agent, or Firm* — Brake Hughes Bellermann LLP (57) ABSTRACT According to an aspect, a penile implant includes a base portion, an extending portion, and an articulating portion. The extending portion being configured to be placed in a first configuration and a second configuration. The extending portion having a first length when the extending portion is in its first configuration. The extending portion having a second length when the extending portion is in its second configuration. The second length being greater than the first length.

19 Claims, 9 Drawing Sheets

FIG. 20

EXTENDABLE PENILE IMPLANT

CROSS-REFERENCE TO RELATED APPLICATION

This application is a Nonprovisional of, and claims priority to, U.S. Patent Application No. 62/745,861, filed on Oct. 15, 2018, entitled "EXTENDABLE PENILE IMPLANT", which is incorporated by reference herein in its entirety.

TECHNICAL FIELD

This disclosure relates generally to bodily implants and more specifically to bodily implants, such as penile prostheses, that may be placed in multiple configurations.

BACKGROUND

One treatment for male erectile dysfunction is the implantation of a penile prosthesis that may be placed in multiple configurations. For example, some existing penile prostheses may be implanted in or near the penis of the patient and may be disposed in a first configuration to place the penis in a flaccid-like state and may be disposed in a second configuration to place the penis in an erect-like state. Some existing implants include complex activation mechanisms to change the configurations of the implants and may require a large amount of effort to change or convert the implant from one configuration to another configuration.

Accordingly, it would be useful to provide a bodily implant, such as a penile prosthesis, that may efficiently be moved from one configuration to another configuration. For example, it would be useful to provide a bodily implant, such as a penile prosthesis, that may be placed in a short configuration and a lengthened configuration.

SUMMARY

According to an aspect, a penile implant includes a base portion, an extending portion, and an articulating portion. The extending portion being configured to be placed in a first configuration and a second configuration. The extending portion having a first length when the extending portion is in its first configuration. The extending portion having a second length when the extending portion is in its second configuration. The second length being greater than the first length.

In some embodiments, the base portion is coupled to the extending portion and the extending portion is coupled to the articulating portion. In some embodiments, the extending portion is disposed between the base portion and the articulating portion.

In some embodiments, the articulating portion is configured to be placed in a curved configuration and a linear configuration. In some embodiments, the articulating portion is configured to be placed in a first configuration and a second configuration, the second configuration being different than the first configuration.

In some embodiments, the extending portion includes a first member and a second member, the first member being movably coupled to the second member. In some embodiments, the extending portion includes a first member and a second member, the first member being slidably coupled to the second member. In some embodiments, the extending portion includes a first member and a second member, the first member defining a cavity, the second member having a portion being configured to be disposed within the cavity defined by the first member.

In some embodiments, the extending portion includes a first member and a second member, the first member including a first engagement portion and a second engagement portion, the second member including a recess, the recess of the second member being configured to engage the first engagement portion when the extending portion is in its first configuration, the recess of the second member being configured to engage the second engagement portion when the extending portion is in its second configuration.

In some embodiments, the extending portion includes a first member and a second member, the first member including a first spring and a second spring, the second member including a recess, the recess of the second member being configured to engage the first spring when the extending portion is in its first configuration, the recess of the second member being configured to engage the second spring when the extending portion is in its second configuration.

In some embodiments, the extending portion includes a first member and a second member, the first member including a first spring and a second spring, the second member including a first recess and a second recess, the first recess of the second member being configured to engage the first spring and the second recess of the second member being configured to engage the second spring when the extending portion is in its first configuration, the first recess of the second member being configured to engage the second spring when the extending portion is in its second configuration.

In some embodiments, the articulating portion includes a first member and a second member, the first member being movably coupled to the second member. In some embodiments, the articulating portion includes a plurality of members configured to move with respect to one another.

In some embodiments, the penile implant includes an outer sheath. In some embodiments, the penile implant includes an outer sheath, the outer sheath housing the base portion, the extending portion, and the articulating portion.

In another implementation, a bodily implant includes a first member, the first member defines a cavity and includes a spring disposed within the cavity; and a second member, the second member defining a receiving portion, the receiving portion being configured to engage the spring to couple the first member to the second member.

In some embodiments, at least a portion of the second member is configured to be disposed within the cavity defined by the first member. In some embodiments, the second member is configured to be removably coupled to the first member.

In another implementation, a method of using a penile implant, includes manipulating an articulating portion of the implant to place the articulating portion in a linear configuration; and manipulating an extending portion of the implant to move the implant from a first configuration to a second configuration, the extending portion having a first length when the implant is in its first configuration and a second length when the extending portion is in its second position, the second length being larger than the first length.

In some embodiments, the manipulating the extending portion includes moving a first member of the extending portion with respect to a second portion of the extending portion.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to medical devices or implants such as penile prostheses or other bodily implants. The term patient or user may hereafter be used for a person who benefits from the medical device or the methods disclosed in the present disclosure. For example, the patient can be a person whose body is implanted with the medical device or the method disclosed for operating the medical device by the present disclosure. For example, in some embodiments, the patient may be a human male, a human female, or any other mammal.

The embodiments discussed herein may improve the performance of a penile prosthesis. For example, the penile prosthesis may have improved usability or functionality. Specifically, in some embodiments, the implant or penile prosthesis may require a small amount of effort to convert the implant from a first configuration to a second configuration. In some embodiments, the implant or penile prosthesis may be able to be placed in a linear and extended or lengthened configuration.

Figure 1:
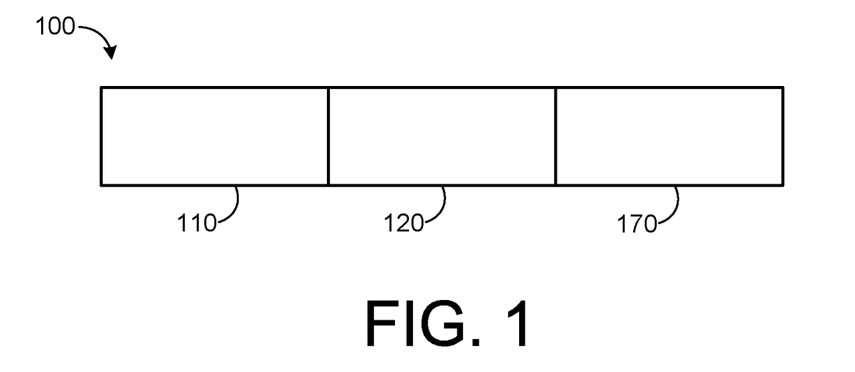
FIG. 1 schematically illustrates an implant, such as a penile prosthesis, according to an embodiment.

FIG. 1 schematically illustrates prosthesis or an implant 100 according to an aspect. The implant includes a base or base portion 110, an extending portion 120, and an articulating portion 170. For example, in some embodiment, the implant 100 may be a penile implant and the implant 100 may be placed within a penis of a patient. Specifically, in some embodiments, the implant 100 may be implanted within the corpus cavernosae of the patient. In other embodiments, the implant may be placed in other locations within the body of the patient.

In some embodiments, more than one implant 100 may be placed within the body of the patient. For example, in some embodiments, two implants 100 may be placed within the body of the patient. Specifically, in some embodiments, two implants 100 may be placed within a penis of the patient. The implants may be placed within the penis of the patient in substantially parallel or a side-by-side arraignment. In other embodiments, only one implant 100 is disposed or implanted within the body of the patient.

The implant 100 may be placed in a variety of configurations. As will be described in more detail below, the implant 100 may be placed in a curved configuration or a linear or substantially linear configuration. Additionally, the implant 100 may be placed in a short configuration or a lengthened configuration. Accordingly, in some embodiments, the implant 100 may be placed within a penis of the patient and the patient may selectively place the implant in (1) a straight or linear configuration to achieve or simulate an erect penis or (2) a curved or non-linear configuration to achieve or simulate a flaccid penis. Additionally, in some embodiments, the implant 100 may be placed within a penis of the patient and the patient may selectively place the implant in (1) a short or retracted configuration or (2) a lengthened or extended configuration.

In the illustrated embodiment, the extending portion 120 is coupled to or extends from the base portion 110 and the articulating portion 170 is coupled to or extends from the extending portion 120. In the illustrated embodiment, the extending portion 120 is disposed between the base portion 110 and the articulating portion 170. In other embodiments, the portions may have different arrangements.

The extending portion 120 is configured to be placed in a first or short configuration and a second or lengthened configuration. In some embodiments, the extending portion 120 includes a first member and a second member. The first member is configured to be moved with respect to the second member to place the extending portion 120 in its first or short configuration or its second or lengthened configuration. In some embodiments, the first and second members include engagement features that are configured to selectively engage with each other to lock or help retain the extending portion 120 in one of its first configuration or its second configuration.

The articulating portion 170 is configured to be placed in a curved configuration and a linear or substantially linear configuration. In some embodiments, the linear or substantially linear configuration has less curve or curvature than when the articulating portion is in its curved configuration. In some embodiments, the articulating portion 170 includes a first member and second member configured to move, pivot, or rotate with respect to the first member. In some embodiments, the second member or the articulating portion 170 is configured to move with respect to the first member of the articulating portion 170 such that the articulating portion 170 may be placed in a curved configuration and a linear or substantially linear configuration. In some embodiments, the articulating portion includes a plurality of members that are configured to move with respect to each other.

In some embodiments, the implant 100 includes a sheath or cover member. In some embodiments, the cover member extends around or surrounds the outer surface of the implant 100. For example, in some embodiments, the cover member defines a cavity and the base portion, the extending portion, and the articulating portion are disposed within the cavity defined by the cover member. In some embodiments, the cover member is coupled to one or more of the base portion, the extending portion, and the articulating portion. In some embodiments, the cover member is flexible and configured to stretch. In such embodiments, the cover member flexes and stretches when the implant 100 is moved from one of its configurations to another of its configurations.

Figure 2:
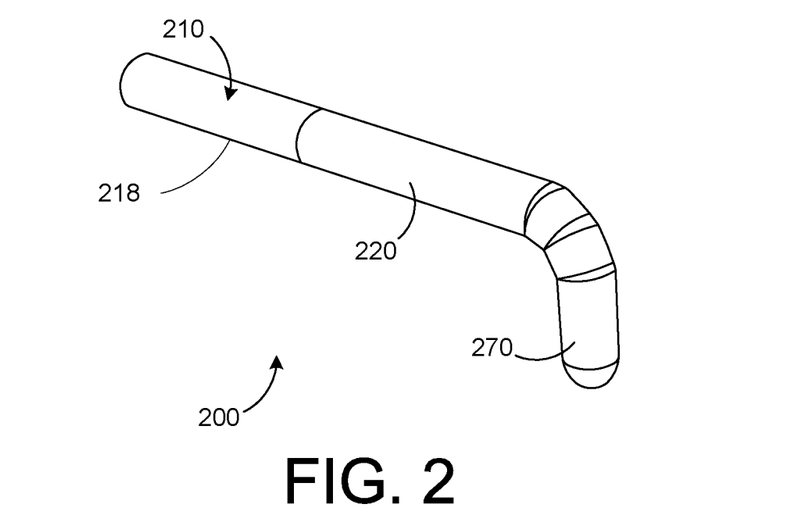
FIG. 2 is a perspective view of a penile prosthesis in a first configuration.
Figure 3:
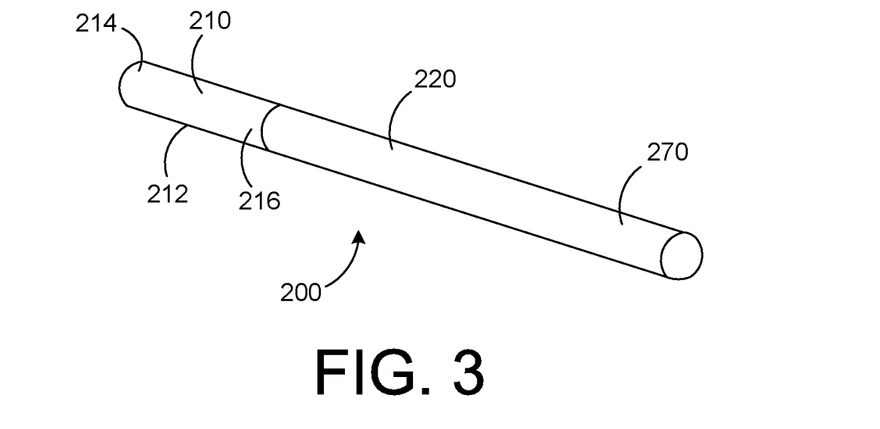
FIG. 3 is a perspective view of the penile prosthesis of FIG. 2 in a second configuration.
Figure 4:
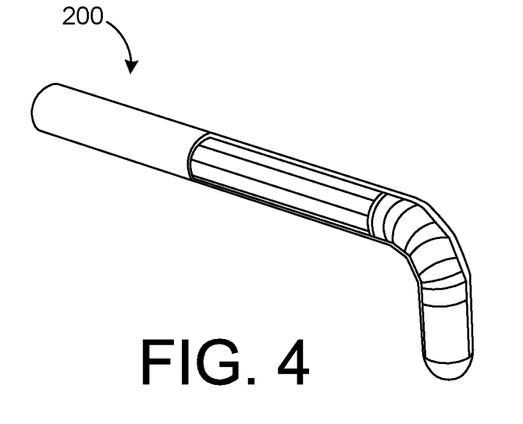
FIG. 4 is a see-through view of the penile prosthesis of FIG. 2 in its first configuration.
Figure 5:
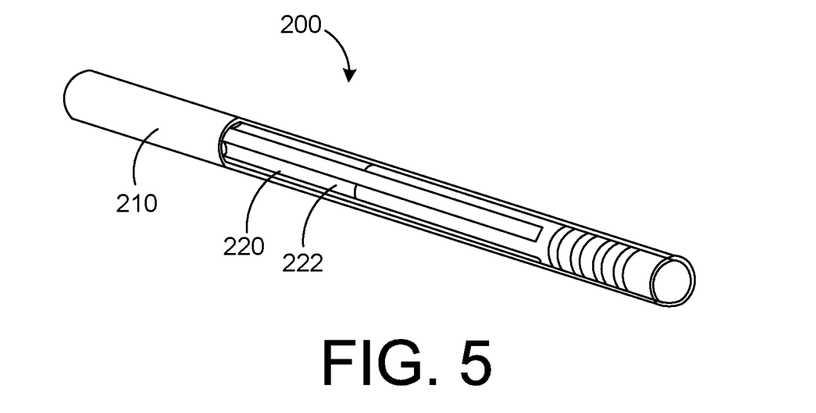
FIG. 5 is a see-through view of the penile prosthesis of FIG. 2 in its second configuration.
Figure 6:
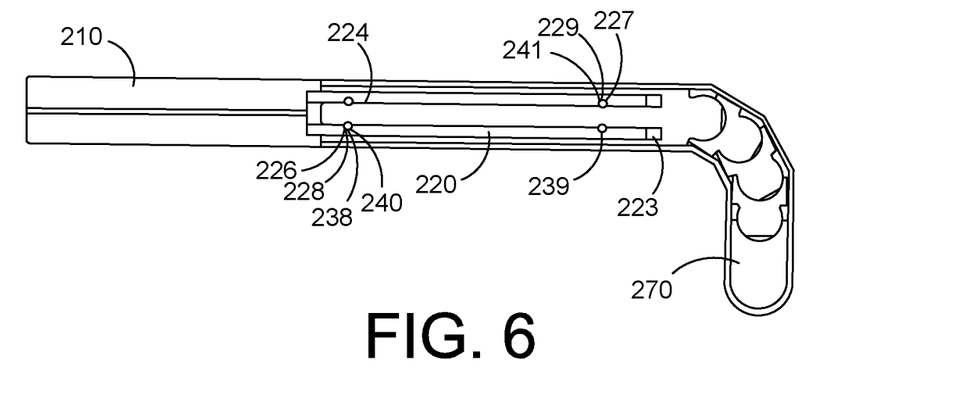
FIG. 6 is a cross-sectional view of the penile prosthesis of FIG. 2 in its first configuration.
Figure 7:
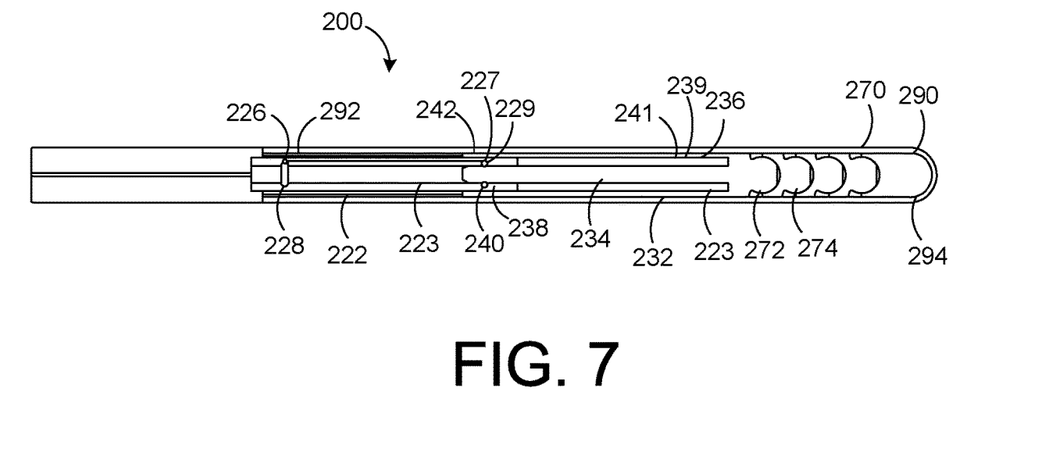
FIGS. 7 and 8 are cross-sectional views of the penile prosthesis of FIG. 2 in its second configuration.
Figure 8:
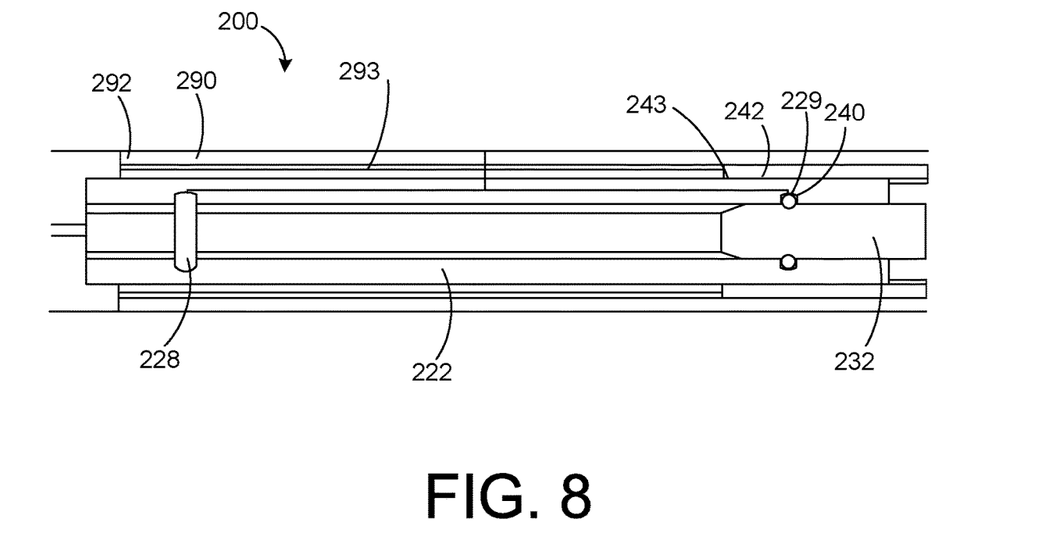

FIGS. 2-8 illustrate an implant or penile prosthesis 200 according to an embodiment. FIG. 2 is a perspective view of the penile prosthesis 200 in a first configuration. FIG. 3 is a perspective view of the penile prosthesis 200 in a second configuration. FIG. 4 is a see-through view of the penile prosthesis 200 in its first configuration. FIG. 5 is a see-through view of the penile prosthesis 200 in its second configuration. In FIGS. 4 and 5, the sheath or cover member is transparent. FIG. 6 is a cross-sectional view of the penile prosthesis 200 in its first configuration. FIGS. 7 and 8 are cross-sectional views of the penile prosthesis 200 in its second configuration.

The implant or penile prosthesis 200 includes a base or base portion 210, an extending portion 220, and an articulating portion 270. For example, in some embodiments, the implant 200 may be placed within a penis of a patient. Specifically, in some embodiments, the implant 200 may be implanted within the corpus cavernosae of the patient. In other embodiments, the implant 200 may be placed in other locations within the body of the patient.

In some embodiments, more than one implant 200 may be placed within the body of the patient. For example, in some embodiments, two implants 200 may be placed within the body of the patient. Specifically, in some embodiments, two implants 200 may be placed within a penis of the patient. The implants may be placed within the penis of the patient in substantially parallel or a side-by-side arraignment. In other embodiments, only one implant 200 is disposed or implanted within the body of the patient.

The implant 200 may be placed in a variety of configurations. As will be described in more detail below, the implant 200 may be placed in a curved configuration or a linear or substantially linear configuration. Additionally, the implant 200 may be placed in a short configuration or a lengthened configuration. Accordingly, in some embodiments, the implant 200 may be placed within a penis of the patient and the patient may selectively place the implant in (1) a straight or linear configuration to achieve or simulate an erect penis or (2) a curved or non-linear configuration to achieve or simulate a flaccid penis. Additionally, in some embodiments, the implant 200 maybe placed within a penis of the patient and the patient may selectively place the implant in (1) a short or retracted configuration or (2) a lengthened or extended configuration.

In the illustrated embodiment, base portion 210 includes a tubular member 212. The tubular member 212 includes a first end portion 214 and a second end portion 216 and has a smooth outer surface 218. In other embodiments, the base portion 210 has a different shape or may include an outer surface that has features or is non-smooth.

The extending portion 220 is coupled to or extends from the base portion 210. Specifically, in the illustrated embodiment, the extending portion 220 is coupled to or extends from the second end portion 216 of the base portion 210. The extending portion 220 is configured to be placed in a first or short configuration and a second or lengthened configuration.

In the illustrated embodiment, the extending portion 220 includes a first member 222 and a second member 232. The first member 222 is configured to be moved with respect to second member 232 to place the extending portion 220 in its first or short configuration (as best illustrated in FIGS. 2, 4, and 6) or its second or lengthened configuration (as best illustrated in FIGS. 3, 5, 7, and 8).

The first member 222 is coupled to or extends from the base portion 210. The first member 222 defines a cavity 223. The cavity 223 is configured to receive a portion of the second member 232. The first member 222 includes an inner surface 224. The inner surface defines the cavity 223.

In the illustrated embodiment, the inner surface 224 of the first member 222 includes a first engagement portion 226 and a second engagement portion 227. The engagement portions 226 and 227 may be any structural form that is configured to engage a portion of the second member 232 to help retain or hold the first member 222 in place with respect to the second member 232.

In the illustrated embodiment, the first engagement portion 226 is a first spring member 228 and the second engagement portion 227 is a second spring member 229. In the illustrated embodiment, the first spring member 228 is a wound or coiled spring member and the second spring member 229 is a wound or coiled spring member. The spring members 228 and 229 are coupled to the inner surface 224 of the first member 222. In some embodiments, an adhesive is used to couple the spring members 228 and 229 to the inner surface 224. In other embodiments, another method of coupling the spring members to the inner surface is used. In the illustrated embodiment, the spring members 228 and 229 extend into the cavity defined by the inner surface 224 of the first member 222.

The second member 232 of the extending portion 220 includes a projection portion 234. The projection portion 234 is configured to be inserted into the cavity 223 defined by the first member 222. The projection portion 234 includes a surface 236. The surface 236 defines engagement features or portions 238 and 239. In the illustrated embodiment, the engagement features or portions 238 and 239 include grooves or depressions 240 and 241.

The engagement features or portions 238 and 239 are configured to engage the spring members 228 and 229 of the first member 222 to help retain the extending portion 220 in its various configurations. Specifically, in the illustrated embodiment, the engagement features or portions 238 and 239 of the second member 232 are configured to engage the engagement portions 226 and 227 of the first member 222 to frictionally retain the extending portion 220 in its configurations. The user may apply force to the device to overcome the frictional retention to move the extending portion 220 from one configuration to another configuration.

FIG. 6 illustrates the extending portion 220 in its collapsed or shortened configuration. In this configuration or position, the first spring 238 engages or is disposed within or partially within the groove 240 and the second spring 239 engages or is disposed within or partially within the groove 241. FIGS. 7 and 8 illustrate the extending portion 220 in its extended or lengthened configuration. In this configuration, the second spring 239 engages or is disposed within or partially within the groove 241.

In the illustrated embodiment, the spring members 228 and 229 extend the entire circumference of the inner surface of the first member and form a complete loop, in other embodiments, the spring members do extend the entire circumference of the inner surface of the first member and do not form a complete loop. In such embodiments, the spring members extend around only a portion of the inner surface.

In the illustrated embodiment, the grooves or depressions 240 and 241 extend around the entire outer surface of the projection portion 234. In other embodiments, the grooves or depressions 240 and 241 do not extend around the entire outer surface of the projection portion 234.

Although in the illustrated embodiment, the engagement portions 226 and 227 of the first member 222 include spring members and the engagement features 238 and 239 of the second member 232 include grooves, in other embodiments, the engagement portions and the engagement features include other structures that are configured to interact or engage with each other. For example, the engagement portions and the engagement features may include ball bearings, ball and socket joints, compression ferrules, interference fit members, detents, pins, rings, slots, keys, cams, clips, clamps, hooks, latches, or any other mechanisms that would allow for coupling, such as a frictional coupling of the first member 222 and the second member 232. Additionally, any number of engagement portions and engagement features may be used.

In the illustrated embodiment, the second member 232 includes an outer portion 242. The outer portion 242 defines a cavity 243. The projection member 234 is disposed within the cavity 243. The cavity 243 is configured to receive at least a portion of the first member 222.

While the illustrated embodiment, the extending portion 220 includes two members (the first member 222 and the second member 232) that are configured to move with respect to each other, in other embodiments, the extending portion 220 includes more than two members that are configured to move with respect to each other. For example, the extending portion may include any number of telescoping members that are configured to be placed in a variety of lengths or configurations.

The articulating portion 270 is coupled to or extends from the extending portion 220. In the illustrated embodiment, the extending portion 220 is disposed between the base portion 210 and the articulating portion 270. In other embodiments, the portions may have different arrangements.

The articulating portion 270 is configured to be placed in a curved configuration (as best illustrated in FIGS. 2, 4, and 6) and a linear or substantially linear configuration (as best illustrated in FIGS. 3, 5, and 7). In some embodiments, the linear or substantially linear configuration has less curve or curvature than when the articulating portion is in its curved configuration.

The articulating portion 270 includes a first member 272 and second member 274 configured to move, pivot, or rotate with respect to the first member 272. The second member 274 of the articulating portion 270 is configured to move with respect to the first member 272 of the articulating portion 270 such that the articulating portion 270 may be placed in a curved configuration and a linear or substantially linear configuration.

In some embodiments, the first member 272 and the second member 274 of the articulating portion 270 include locking features that allow the first member 272 and the second 274 to be moved into and locked or frictionally coupled into a curved or linear configuration.

The articulating portion 270 of the implant 200 includes a plurality or more than two members that are configured to move with respect to each other. In other embodiments, the articulating portion 270 includes any number of members that are configured to move and interact with each other to place the articulating portion 270 in a curved configuration or a linear or substantially linear configuration.

The implant 200 includes a sheath or cover member 290. The cover member 290 extends around or surrounds the outer surface of the implant 200. For example, in some embodiments, the cover member 290 defines a cavity 293 and the base portion 210, the extending portion 220, and the articulating portion 270 are disposed within the cavity 293 defined by the cover member 290.

In the illustrated embodiment, the cover member 290 includes a first end portion 292 that is coupled to the base portion 210 and a second end portion 294 that is coupled to the articulating portion 270. In other embodiments, the cover member is coupled to the implant at different locations. The cover member 290 is flexible and configured to stretch. In such embodiments, the cover member 290 flexes and stretches when the implant 200 is moved from one of its configurations to another of its configurations.

Figure 9:
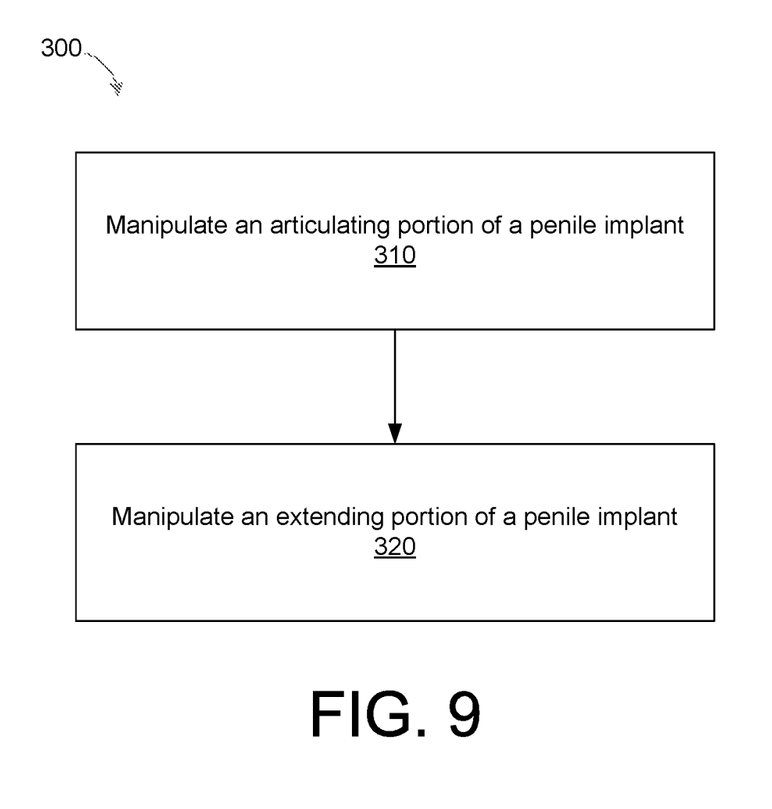
FIG. 9 is a flow chart of a method according to an embodiment.

In use, the implant 200 may be inserted into the body of a patient. For example, in some embodiments, the implant 200 may be a penile implant and may be inserted or implanted into a penis of the patient. FIG. 9 is a flow chart of a method 300 according to an embodiment. At 310, when a patient wishes to have an erect penis, the user or patient may move or manipulate the articulating portion to move the articulating portion from a first or curved configuration to a linear or substantially linear configuration. The patient may do this by grasping or manipulating the implant through bodily tissue such as the bodily tissue of the penis. At 320, the patient may pull or place a pulling force on the implant 200 to move the extending portion of the implant 200 from a first or shortened configuration to a long or lengthened configuration.

Once the patient no longer wishes to have an erect penis, the patient may manipulate the articulating portion and the extending portion to return the implant to its shortened and curved configuration.

Figure 10:
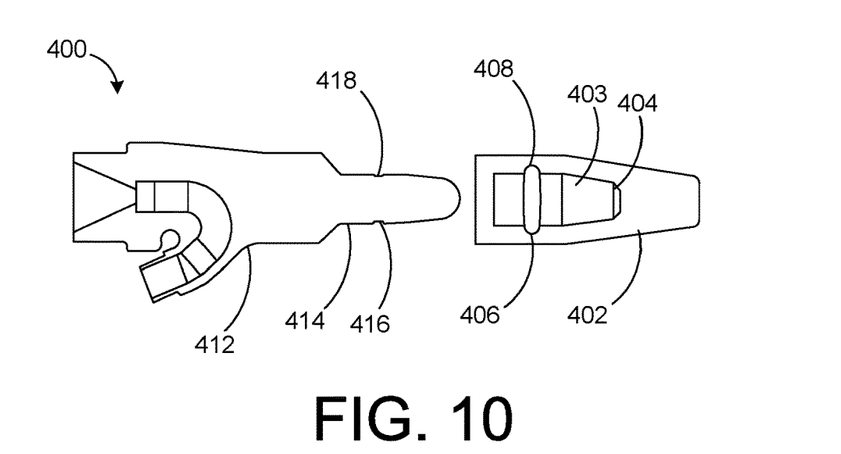
FIGS. 10 and 11 are cross-sectional views of a portion of an implant according to another embodiment.
Figure 11:
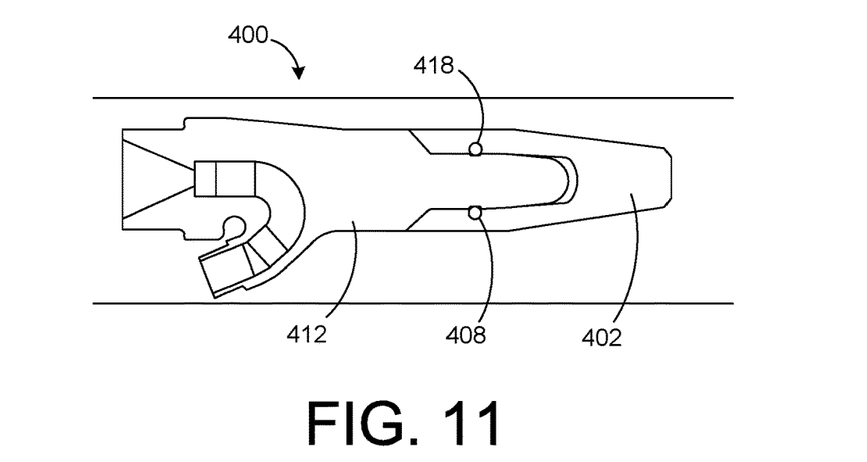

FIGS. 10 and 11 illustrate an implant 400 according to an embodiment of the invention. The implant 400 is a bodily implant and in some embodiments, may be configured to be placed within a penis of a patient. In the illustrated embodiment, the implant 400 includes a first portion 402 and a second portion 412. In some embodiments, the first portion 402 may be a tip extender for a penile implant such as a rear tip extender. The first portion 402 is configured to be coupled to the second portion 412 of the device 400.

In the illustrated embodiment, the first portion 402 defines a cavity 403. The cavity 403 is configured to receive at least a portion of the second portion 412. The first portion 402 includes an inner surface 404 that defines the cavity 403. The first portion 402 includes an engagement portion 406. In the illustrated embodiment, the engagement portion 406 is a spring member 408. The spring member 408 is a wound or coiled spring member 408.

The second portion 412 includes a projection portion 414 that is configured to be inserted into the cavity 403 of the first portion 402. The projection portion 414 includes an engagement portion 416. The engagement portion 416 is configured to engage the spring member 408 to couple the first portion 402 to the second portion 412. In the illustrated embodiment, the engagement portion 416 includes a groove or depression 418.

In use the projection portion 414 can be inserted into the cavity 403 such that the spring member 408 engages the groove or depression 418 to couple the first portion 402 to the second portion 412. FIG. 10 illustrates the first portion 402 and the second portion 412 in an uncoupled configuration. FIG. 11 illustrates the first portion 402 coupled to the second portion 412.

Figure 12:
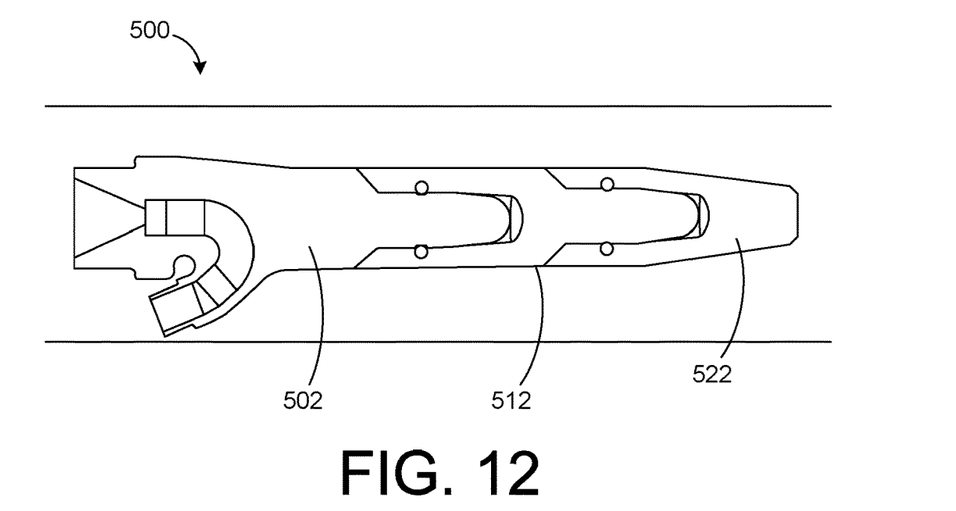
FIG. 12 is a cross-sectional view of a portion of an implant according to another embodiment.

As illustrated in FIG. 12, in some embodiments, the implant 500 includes more than one members or portions that can be coupled together. The illustrated implant 500 includes a first portion 502, a second portion 512, and a third portion 522. Any number of portions, such as tip extenders, can be used.

Figure 13:
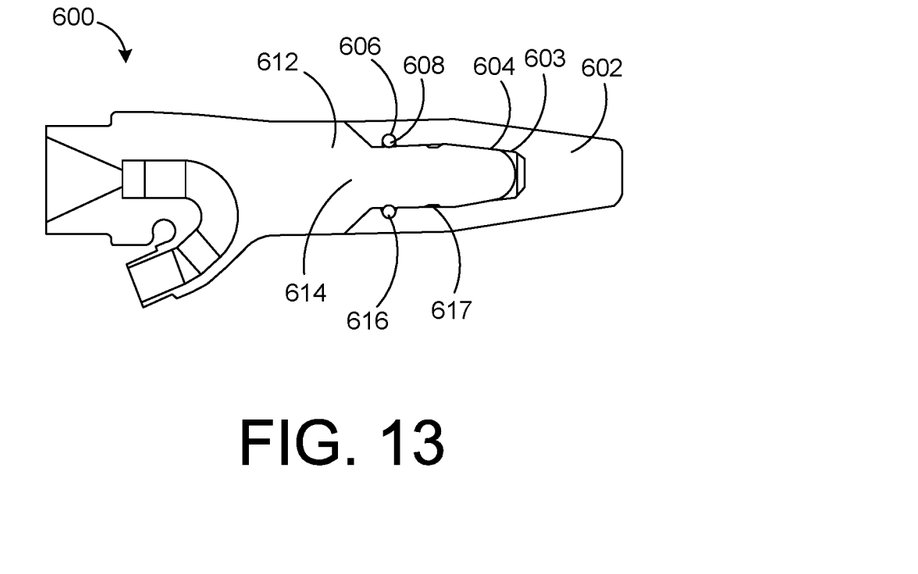
FIG. 13 is a cross-sectional view of a portion of an implant according to another embodiment in a first configuration.
Figure 14:
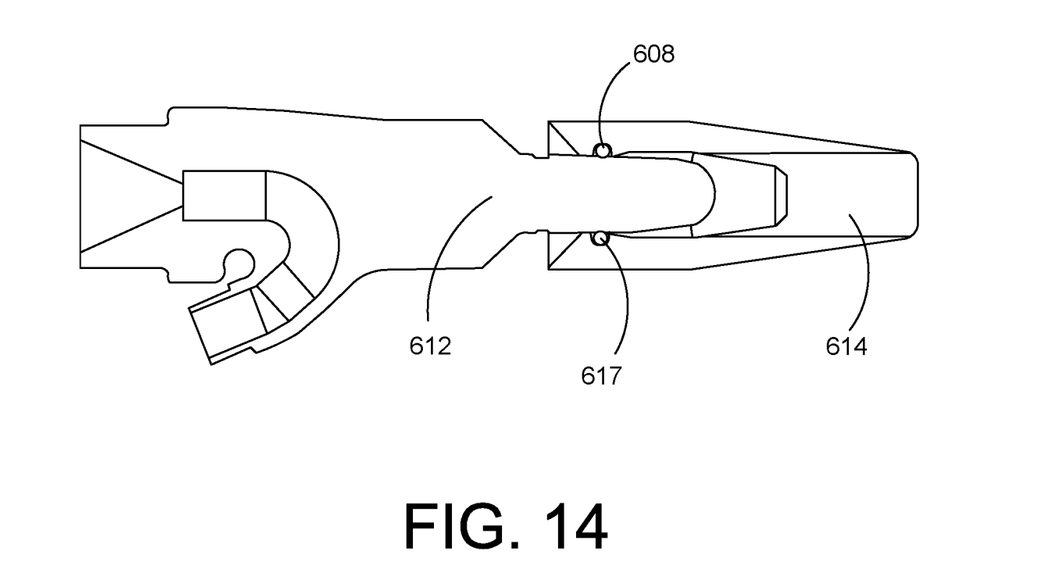
FIG. 14 is a cross-sectional view of a portion of the implant of FIG. 13 in a second configuration.

FIGS. 13 and 14 illustrate an implant 600 according to an embodiment of the invention. The implant 600 is a bodily implant and in some embodiments, may be configured to be placed within a penis of a patient. In the illustrated embodiment, the implant 600 includes a first portion 602 and a second portion 612. In some embodiments, the first portion 602 may be a tip extender for a penile implant such as a rear tip extender. The first portion 602 is configured to be coupled to and adjustable with respect to the second portion 612 of the device 600. Said another way, the first portion 602 is configured to be coupled to the second portion 612 at a first position or configuration and at a second position or configuration.

In the illustrated embodiment, the first portion 602 defines a cavity 603. The cavity 603 is configured to receive at least a portion of the second portion 612. The first portion 602 includes an inner surface 604 that defines the cavity 603. The first portion 602 includes an engagement portion 606. In the illustrated embodiment, the engagement portion 606 is a spring member 608. The spring member 608 is a wound or coiled spring member 608.

The second portion 612 includes a projection portion 614 that is configured to be inserted into the cavity 603 of the first portion 602. The projection portion 614 includes a first engagement portion 616 and a second engagement portion 617. The engagement portions 616 and 617 are configured to engage the spring member 608 to couple the first portion 602 to the second portion 612. In the illustrated embodiment, the engagement portions 616 and 617 include grooves or depressions.

In use the projection portion 614 can be inserted into the cavity 603 such that the spring member 608 engages the groove or depression 618 or the groove or depression 617 to couple the first portion 602 to the second portion 612. FIG. 13 illustrates the first portion 602 coupled to the second portion 612 at a first position. FIG. 14 illustrates the first portion 602 coupled to the second portion 612 at a second position.

Figure 15:
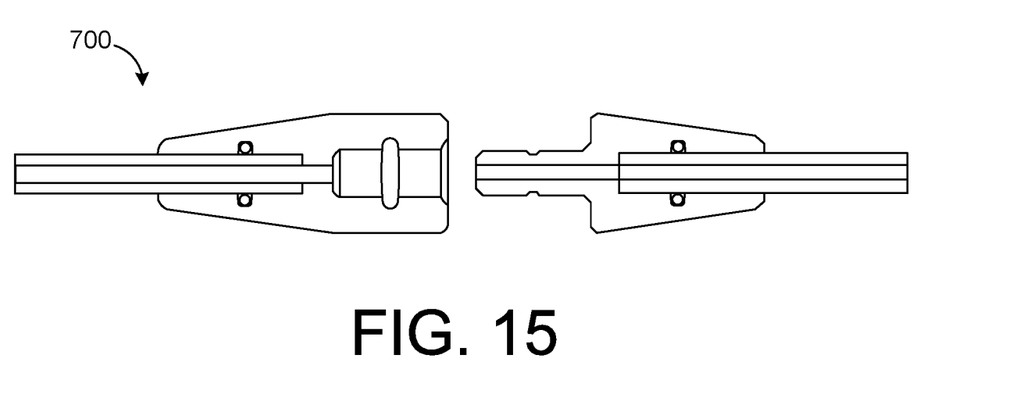
FIG. 15 is a cross-sectional view of a portion of an implant according to another embodiment in a disconnected configuration.
Figure 16:
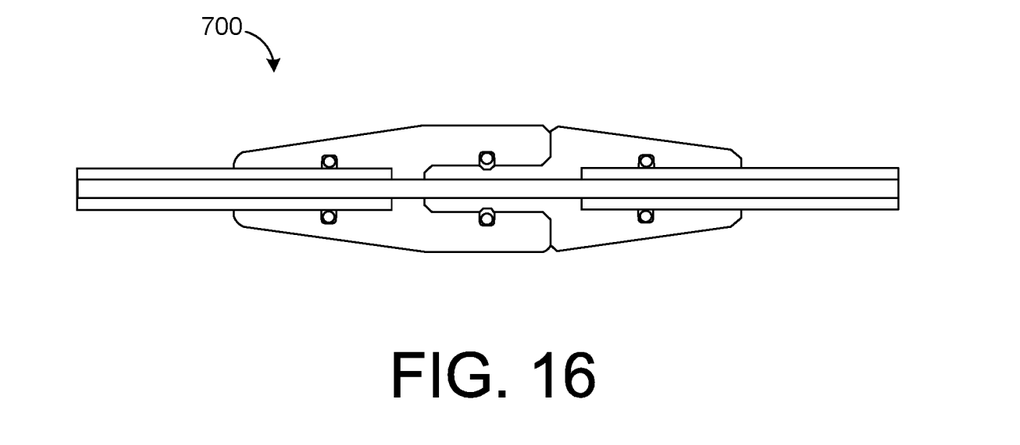
FIG. 16 is a cross-sectional view of a portion of the implant of FIG. 15 in a connected configuration.

FIGS. 15 and 16 illustrate an implant, such as a connector or a tool-less connector, 700 that may be coupled using a wound spring and groove connection.

Figure 17:
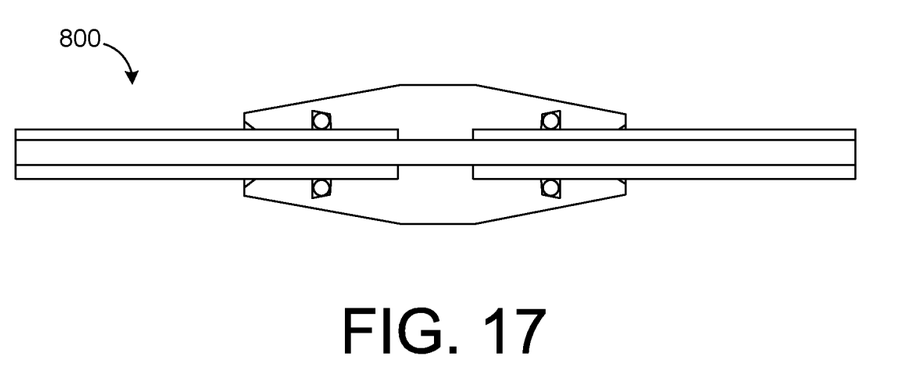
FIGS. 17 and 18 are cross-sectional views of a portion of an implant according to another embodiment.
Figure 18:
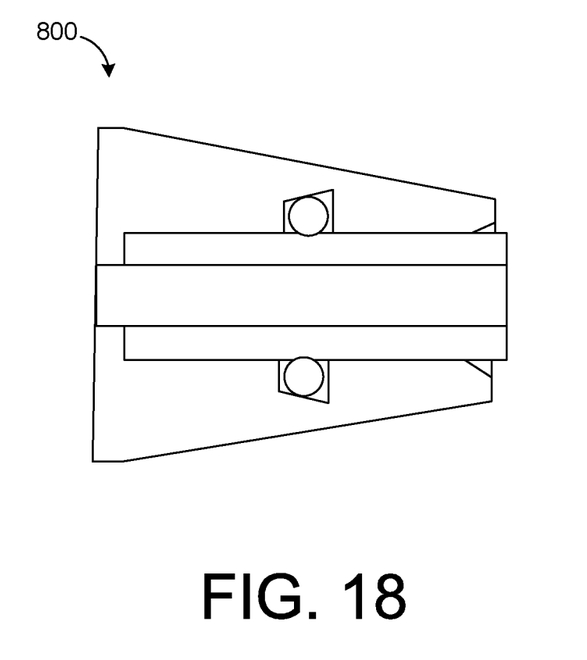

FIGS. 17 and 18 illustrate a one-piece connector 800 that includes a spring and groove couplings.

Figure 19:
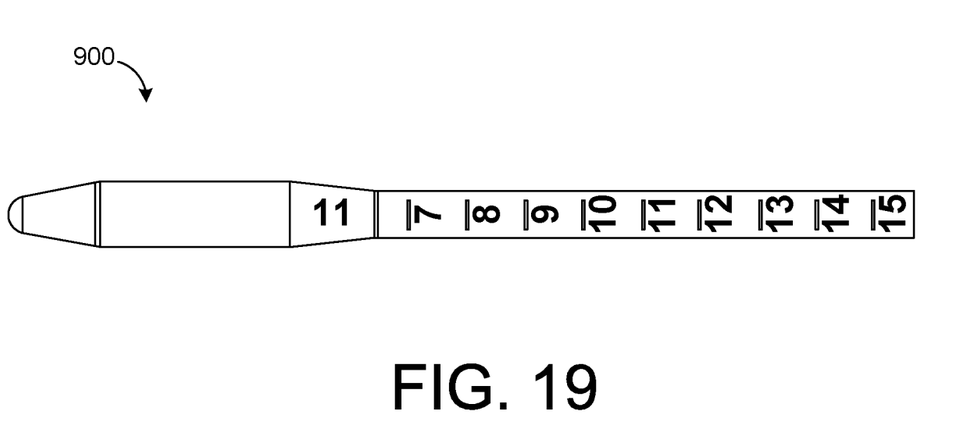
FIG. 19 is a side view of a dilator according to another embodiment.
Figure 20:
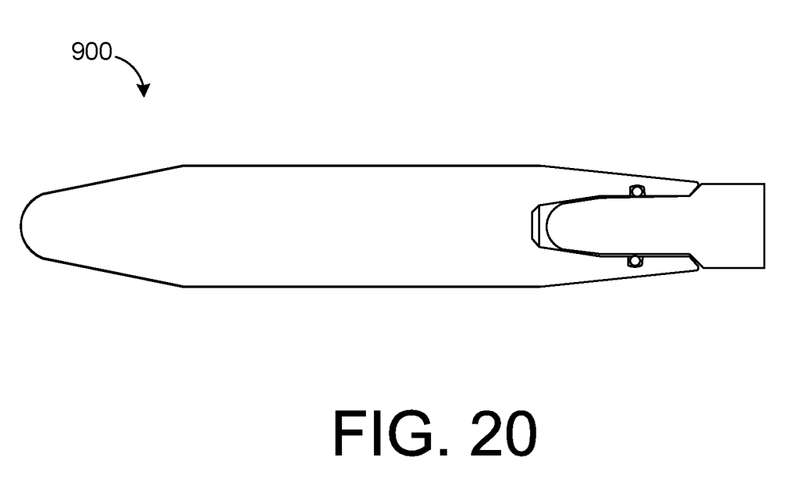
FIG. 20 is a cross-sectional view of the dilator of FIG. 19.

FIGS. 19 and 20 illustrate a dilator 900 that includes a spring and groove coupling.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A penile implant, comprising:
   a base portion;
   an extending portion, the extending portion being configured to be placed in a first configuration and a second configuration, the extending portion having a first length when the extending portion is in the first configuration, the extending portion having a second length when the extending portion is in the second configuration, the second length being greater than the first length, the extending portion including a first member and a second member, the first member including an engagement portion, the second member including a recess, the recess of the second member being configured to engage the engagement portion when the extending portion is in one of the first configuration and the second configuration; and
   an articulating portion.

2. The penile implant of claim 1, wherein the base portion is coupled to the extending portion and the extending portion is coupled to the articulating portion.

3. The penile implant of claim 1, wherein the extending portion is disposed between the base portion and the articulating portion.

4. The penile implant of claim 1, wherein the articulating portion is configured to be placed in a curved configuration and a linear configuration.

5. The penile implant of claim 1, wherein the articulating portion is configured to be placed in a third configuration and a fourth configuration, the fourth configuration being different than the third configuration.

6. The penile implant of claim 1, wherein the first member is movably coupled to the second member.

7. The penile implant of claim 1, wherein the first member is slidably coupled to the second member.

8. The penile implant of claim 1, wherein the first member defines a cavity, the second member having a portion being configured to be disposed within the cavity defined by the first member.

9. The penile implant of claim 1, wherein the engagement portion is a first engagement portion, the first member including a second engagement portion, the recess of the second member being configured to engage the first engagement portion when the extending portion is in the first configuration, the recess of the second member being configured to engage the second engagement portion when the extending portion is in the second configuration.

10. The penile implant of claim 1, wherein the articulating portion includes a first member and a second member, the first member of the articulating portion being movably coupled to the second member of the articulating portion.

11. The penile implant of claim 1, wherein the articulating portion includes a plurality of members configured to move with respect to one another.

12. The penile implant of claim 1, further comprising:
    an outer sheath.

13. The penile implant of claim 1, further comprising:
    an outer sheath, the outer sheath housing the base portion, the extending portion, and the articulating portion.

14. The penile implant of claim 1, wherein the engagement portion includes a spring.

15. A method of using a penile implant, comprising:
manipulating an articulating portion of the implant to place the articulating portion in a linear configuration; and
manipulating an extending portion of the implant to move the implant from a first configuration to a second configuration, the extending portion having a first length when the implant is in the first configuration and a second length when the extending portion is in the second configuration, the second length being larger than the first length, the manipulating the extending portion including sliding a first member of the extending portion with respect to a second member of the extending portion, the manipulating the extending portion including engaging an engaging portion of the first member with a recess of the second member.

16. A penile implant, comprising:
an extending portion, the extending portion being configured to be placed in a first configuration and a second configuration, the extending portion having a first length when the extending portion is in the first configuration, the extending portion having a second length when the extending portion is in the second configuration, the second length being greater than the first length, the extending portion including a first member and a second member, the first member including a first spring and a second spring, the second member including a first recess and a second recess, the first recess of the second member being configured to engage the first spring and the second recess of the second member being configured to engage the second spring when the extending portion is in the first configuration, the first recess of the second member being configured to engage the second spring when the extending portion is in the second configuration; and
an articulating portion.

17. The penile implant of claim 16, wherein the articulating portion includes a first member and a second member, the first member of the articulating portion being movably coupled to the second member of the articulating portion.

18. The penile implant of claim 16, wherein the articulating portion includes a plurality of members configured to move with respect to one another.

19. The penile implant of claim 16, further comprising:
an outer sheath.

* * * * *